United States Patent
Smith et al.

(10) Patent No.: US 9,452,125 B2
(45) Date of Patent: Sep. 27, 2016

(54) SELF-TANNING COMPOSITIONS HAVING REDUCED MAILLARD REACTION MALODOR

(75) Inventors: Alisa Ivory Smith, Cincinnati, OH (US); Jordan Cordeiro, Liberty Township, OH (US); Jessica Rustici-Jones, Covington, KY (US)

(73) Assignee: Kao USA Inc., Cincinnati, OH (US)

( * ) Notice: Subject to any disclaimer, the term of this patent is extended or adjusted under 35 U.S.C. 154(b) by 0 days.

(21) Appl. No.: 13/451,996

(22) Filed: Apr. 20, 2012

(65) Prior Publication Data

US 2012/0269743 A1    Oct. 25, 2012

Related U.S. Application Data

(60) Provisional application No. 61/477,383, filed on Apr. 20, 2011.

(51) Int. Cl.
| | |
|---|---|
| *A61K 8/73* | (2006.01) |
| *A61Q 19/04* | (2006.01) |
| *A61K 8/92* | (2006.01) |
| *A61K 8/35* | (2006.01) |

(52) U.S. Cl.
CPC ............... *A61K 8/732* (2013.01); *A61K 8/35* (2013.01); *A61Q 19/04* (2013.01)

(58) Field of Classification Search
CPC .......... A61K 8/00; A61K 8/06; A61K 8/062; A61K 8/30; A61K 8/732
See application file for complete search history.

(56) References Cited

U.S. PATENT DOCUMENTS

| | | | |
|---|---|---|---|
| 2,949,403 A | 8/1960 | Andreadis et al. | |
| 3,177,120 A | 4/1965 | Black et al. | |
| 4,434,154 A | 2/1984 | McShane | |
| 4,708,865 A | 11/1987 | Turner | |
| 5,232,688 A | 8/1993 | Ziegler et al. | |
| 5,252,322 A | 10/1993 | Stoner et al. | |
| 5,514,367 A | 5/1996 | Lentini et al. | |
| 5,614,178 A | 3/1997 | Bloom et al. | |
| 6,268,353 B1 | 7/2001 | Chaen et al. | |
| 2006/0045857 A1 | 3/2006 | Roszell | |
| 2006/0148757 A1 | 7/2006 | Oku et al. | |
| 2007/0003585 A1* | 1/2007 | Clark et al. | 424/401 |
| 2008/0003245 A1 | 1/2008 | Kroepke | |
| 2008/0058738 A1 | 3/2008 | Roberts et al. | |
| 2009/0155322 A1* | 6/2009 | Harichian et al. | 424/401 |
| 2009/0226386 A1 | 9/2009 | Brillouet et al. | |

FOREIGN PATENT DOCUMENTS

| | | |
|---|---|---|
| FR | 2840806 | 12/2003 |
| WO | WO 2007/060021 | 5/2007 |

OTHER PUBLICATIONS

International Search Report and Written Opinion dated Nov. 8, 2013 for Application No. PCT/US2012/034468, 9 pgs.
Australian Office Action dated May 19, 2016 for Application No. AU 2012245274, 3 pgs.

* cited by examiner

*Primary Examiner* — Mina Haghighatian
*Assistant Examiner* — Luke Karpinski
(74) *Attorney, Agent, or Firm* — Frost Brown Todd LLC

(57) ABSTRACT

The present invention provides novel cosmetic compositions for artificially tanning the skin, utilizing skin-tanning agents and odor-mitigating materials, such as specifically defined starch materials. The compositions reduce the undesirable odors associated with the reaction between the skin-tanning agents, such as dihydroxyacetone, and the skin (chemically known as the Maillard reaction). The method of using those compositions and of formulating those compositions is also disclosed.

17 Claims, No Drawings

SELF-TANNING COMPOSITIONS HAVING REDUCED MAILLARD REACTION MALODOR

This application is related to and claims priority from U.S. Provisional Patent Application Ser. No. 61/477,383, Smith et al., filed Apr. 20, 2011, incorporated herein by reference.

TECHNICAL FIELD

This invention relates to compositions for providing an artificial tan to skin and methods for their preparation and use. More specifically, the invention relates to skin-tanning compositions which comprise a skin-tanning agent and one or more odor-mitigating materials (such as an expanded starch-based polysaccharide containing at least about 50% amylopectin) in a cosmetically-acceptable carrier.

BACKGROUND

Many individuals have a skin complexion which does not tan readily on exposure to sunlight. Others achieve a tan only with great discomfort and possibly adverse effects to the skin due to exposure to sun's rays, e.g., sunburn. Yet, attainment of a tan is highly desired by many individuals for cosmetic and other reasons, especially if this can be accomplished effectively without the usual exposure to the sun, i.e., through skin-tanning agents.

In other instances, individuals who tan with difficulty may desire to enhance or extend the life of a naturally acquired tan without re-exposure to the sun. Also, a suntan may be desired when weather conditions do not permit the sun exposure necessary to acquire a tan.

Acquisition of a natural tan by exposure to the sun may be almost impossible for those very light skin persons who tend to burn rather than tan. In addition, the deleterious effects of excessive exposure to sunlight are becoming more generally recognized.

It is known in the art that an artificial tan can be achieved by applying skin-tanning agents to the human skin in a suitable vehicle or base. Examples of known skin-tanning agents include hydroxyaldehydes, such as dihydroxyacetone, see U.S. Pat. Nos. 2,949,403 and 5,232,688. Also known as skin-tanning agents are imidazole and various imidazole derivatives, such as 4-(hydroxymethylimidazole); see U.S. Pat. No. 5,252,322, Stoner et al, issued Oct. 12, 1993.

U.S. Pat. No. 2,949,403, Andreadis et al, issued Aug. 16, 1960, discloses compositions of and methods of using dihydroxyacetone as a tanning agent for the human epidermis. It has been reported that dihydroxyacetone reacts with skin proteins and amino acids to elicit its skin coloring effect. Since the 1960s, several compositions using dihydroxyacetone as an active ingredient have been reported. These compositions include a topical composition containing dihydroxyacetone and various dyes, such as catch powder, dogwood powder and walnut powder (the dyes are employed to offset the undesirable orange cast or hue which results from the use of dihydroxyacetone on fair skinned humans, see U.S. Pat. No. 4,708,865, Turner, issued Nov. 24, 1987). These also include compositions containing dihydroxyacetone and sunscreen compounds, such as octyl dimethyl PABA (see, for example, U.S. Pat. No. 4,434,154, McShane, issued Feb. 28, 1984, and U.S. Pat. No. 3,177,120, Black et al, issued Apr. 6, 1965). Further, dihydroxyacetone has been formulated into oil-in-water emulsions, into preparations containing up to 50% alcohol which tend to dry the skin, and into "creamy bases", such as are found in hand and face lotions and creams.

U.S. Pat. No. 5,232,688, Ziegler et al, issued Aug. 3, 1993, discloses compositions for self-tanning of skin which include an alpha-hydroxy substituted ketone or aldehyde, such as dihydroxyacetone or erythrulose, a polyacrylamide, and a pharmaceutically-acceptable carrier.

U.S. Pat. No. 5,514,367, Lentini et al (assigned to Estee Lauder), issued May 7, 1996, describes self-tanning compositions which include a self-tanning agent (such as dihydroxyacetone) together with cyclodextrin. These compositions are said to improve storage stability and prevent the formation of Maillard reaction odors during use of the composition.

U.S. Pat. No. 6,268,353, Chaen et al, issued Jul. 31, 2001, describes the use of trehalose and/or maltitol to prevent the formation of odiferous aldehydes and fatty acid decomposition products in food products, as well as in body lotions. This patent does not describe the use of self-tanning products or the Maillard reaction odors resulting from the topical use of such compositions.

U.S. Published Patent Application 2006/0148757, Oku, published Jul. 6, 2006, uses α-oligoglucosyl-α,α-trehalose to prevent the formation of volatile aldehyde and fatty acid decomposition products which can form odors in food and skin lotion products. This application is related to U.S. Pat. No. 6,268,353, discussed above.

U.S. Published Patent Application 2008/0003245, Kroepke et al, published Jan. 30, 2008, describes cosmetic compositions which include 1,3-dihydroxyacetone (DHA) together with octyl salicylate. The purpose of these compositions is to stabilize the DHA in the composition.

U.S. Published Patent Application 2008/0058738, Roberts et al, published Mar. 6, 2008, describes the use of expanded starch particles combined with transition metals to absorb and bind odor molecules in absorbent articles.

PCT Published Patent Application WO 2007/060021, Brillouet et al, published May 31, 2007, describes compositions which are used to stabilize dihydroxyacetone in product in order to prevent the formation of odiferous decomposition products. These self-tanning compositions include a self-tanning agent, such as dihydroxyacetone, a modified starch gelling agent, and optionally a branched polysaccharide gelling agent.

While dihydroxyacetone has been widely employed as a skin-tanning agent, commercial preparations containing dihydroxyacetone suffer from a number of drawbacks. One such disadvantage is the physical and chemical degradation of dihydroxyacetone-containing preparations over extended periods of time, for example, during warehouse storage or after consumer purchase. Such degradation leads to discoloration, the development of unpleasant odors, and an overall loss of stability and skin-tanning efficiency. Several of the references discussed above attempt to address this concern. A further disadvantage of such preparations is the development of aesthetically-unacceptable odors following application of such preparations to the skin. This is thought to occur as the result of the Maillard reaction, a reaction between dihydroxyacetone and the skin which results in skin-tanning. It is this latter concern which the present invention addresses.

SUMMARY

All percentages and ratios given herein are "by weight", unless otherwise specified. Further, all patents, patent applications and texts cited in this application are incorporated herein by reference.

The present invention relates to skin-tanning compositions which comprise:
(a) an effective amount of a skin-tanning agent (such as dihydroxyacetone (DHA) or erythrulose);
(b) from about 0.1% to about 10% of an odor-mitigating compound selected from expanded starch-based polysaccharides that contain at least about 50% amylopectin (such as waxy corn starch or a modified starch such as aluminum starch octenylsuccinate); and
(c) a cosmetically-acceptable carrier.

These compositions are stable and provide an artificial tan to the human skin while reducing malodors caused by use of the self-tanning agents.

This invention also encompasses a method of providing an artificial tan to human skin which comprises applying an effective amount of the compositions defined herein to the skin.

The present invention also relates to a method of reducing the Maillard reaction odor generated when a sunless tanning composition, containing a self-tanning agent, such as dihydroxyacetone, is applied to the skin, comprising including in said composition from about 0.1% to about 10% of an odor-mitigating compound selected from expanded (processed) starch-based polysaccharides that contain at least about 50% amylopectin (such as waxy corn starch and/or a modified starch such as aluminum starch octenylsuccinate).

Finally, the present invention relates to a process for making the skin-tanning compositions defined herein.

DETAILED DESCRIPTION

As mentioned above, the present invention provides skin-tanning compositions comprising:
(a) an effective amount of a skin-tanning agent;
(b) from about 0.1% to about 10% of an odor-mitigating material selected from expanded starch-based polysaccharides that contain at least about 50% amylopectin; and
(c) a cosmetically-acceptable carrier.

The skin-tanning compositions of the present invention are cosmetic compositions suitable for topical application to animals, particularly humans. The cosmetic compositions are particularly suitable for topical application in the form of, including, but not limited to, emulsions, lotions, gels, sprays, foams, wipes, liquids, solids or powders.

As described herein, the main components of these skin-tanning compositions are a skin-tanning agent, and an odor-mitigating compound (such as an expanded (processed) starch material, as defined herein), in a cosmetically-acceptable carrier. Clearly, various optional ingredients frequently used in topical formulations, including, but not limited to, penetration enhancers, fragrances, preservatives, emulsifiers, anti-bacterials, pigments, dyes, humectants, propellants, emollients, and stabilizers, as well as other classes of materials whose presence may be cosmetically, medicinally or otherwise desirable, can also be included in these compositions. It is essential, however, to include at least one skin-tanning agent and at least one odor-mitigating compound in a cosmetically-acceptable carrier to achieve the benefits that the compositions of the present invention can provide.

As used herein and in the relevant art, a skin-tanning agent is a material that is capable of coloring the skin through chemical reaction; in particular, a material capable of darkening the skin so that it resembles the darkening effect achieved by exposure of one's skin to the sun's rays (i.e., a natural tan). Several skin-tanning agents are known in the cosmetic art. Any of these can be used in the present invention. For example, α-hydroxy aldehydes may be used, including, but not limited to, dihydroxyacetone (DHA), erythrulose, and derivatives thereof. Similarly, imidazole and imidazole derivatives can be used. Dihydroxyacetone and erythrulose are preferred, however, with dihydroxyacetone being particularly preferred.

The skin-tanning agent is included in the composition in an effective amount. By "effective amount" is meant that amount which provides effective skin coloration, mimicking a natural suntan, but not so much as to miscolor the skin or result in side effects, such as skin irritation or dermatitis. In one embodiment of the present invention, an effective amount of a skin-tanning agent is from about 0.1% to about 20%, preferably from about 0.1% to about 10%, more preferably from about 1% to about 10%, of the total weight of the composition.

The self-tanning products of the present invention can be optimized for use on one or multiple skin-tones, providing a defined level of skin coloration, based on descriptions and characteristics of particular skin-tones, such as light, fair, medium, fair/medium, medium/tan and tan/dark.

In a preferred embodiment of the present invention, the skin-tanning agent is dihydroxyacetone (DHA). Dihydroxyacetone is available, for example, from Napp Technologies (Hackensack, N.J.) or E. Merck and Company (Darmstadt, Germany). An effective amount of dihydroxyacetone is from about 0.1% to about 20% of the total composition, preferably from about 0.1% to about 10% of the composition.

The second required element of the compositions of the present invention is an odor-mitigating component selected from expanded (processed) starch-based polysaccharides that contain at least about 50% amylopectin. Mixtures of such materials can be used herein. Such materials are typically included in the present compositions at from about 0.1% to about 10%, preferably from about 1% to about 10% or from about 2% to about 8%, and more preferably from about 3% to about 7%, of the total composition. While starch materials have been included in topical formulations before, they typically have not been processed to provide an expanded, non-crystalline structure, and have been used for their rheological or skin-feel effects, and not for the purpose of minimizing Maillard reaction odors which are caused by the use of self-tanning agents on the skin.

The starches useful in the present invention are those which contain at least about 50%, preferably at least about 70% (by weight), amylopectin. These polysaccharides can be either modified or unmodified and should be capable of releasing amylopectin upon heating. Starch is a major form of carbohydrates; it is composed of a mixture of two substances: amylose, an essentially linear polysaccharide, and amylopectin, a highly branched polysaccharide. In amylopectin, glucose units are linked in a linear way with α (1-4) glucose bonds. Branching takes place with α (1-6) bonds occurring every 24 to 30 glucose units, resulting in a soluble molecule that can be quickly degraded, since it has many end points for enzymes to attach to. In contrast, amylose contains very few a (1-6) bonds, which causes it to be hydrolyzed more slowly, but have higher density and be insoluble.

Examples of starches useful in the present invention include waxy maize starch, rice starch, tapioca starch, potato starch, maize starch (eg, aluminum starch octenylsuccinate, Akzo Nobel Purity 21 C, Sigma Aldrich S9679 amylopectin), sago starch, wheat starch, and mixtures of those materials. Particularly preferred starches include waxy maize, or maize with an amylopectin level of at least about 70%.

The starches utilized in the present invention are processed ("cooked" or "expanded") which may release amylopectin contained in the starch, breaks down the crystal structure of the starch, and provides for more significant odor reduction performance. The effects of this processing can be seen when the starch granules in the formulation are viewed using a microscope (e.g., 1000×) under polarized light: the unprocessed starch granules have a visible Maltese Cross structure, which is characteristic of their crystalline birefringence pattern, while the processed starches do not. Such processed or expanded starch materials are described in U.S. Published Patent Application 2008/0058738, Roberts et al, published Mar. 6, 2008 (see especially paragraphs [0021]-[0024]), incorporated herein by reference. As a general procedure, the starch material is processed by placing it in a solvent (such as water) and heated to a temperature of from about 50° C. to about 90° C. (preferably from about 70° C. to about 80° C.) for a period of from about 5 minutes to about 24 hours (preferably from about 10 minutes to about 60 minutes). Pregelatinized Starch, a component well-known in the pharmaceutical formulation art (see the Handbook of Pharmaceutical Excipients, Rowe (editor), Royal Pharmaceutical Society, UK), is chemically or mechanically processed to rupture all or part of the starch granules, does not have the typical starch crystal structure, and may be used as the odor-mitigating material herein.

The starch may be irradiated prior to use to reduce the microbial load in the final compositions.

The term "cosmetic carrier", as used herein, includes any vehicle or base which is capable of delivering the skin-tanning agent and odor-mitigating material to the skin, and which does not irritate or cause other negative effects to the skin. The cosmetically-acceptable carrier can be in the form of, for example, a spray, mist, cream, lotion, gel, powder, mask, solution, emulsion, body wash or other surfactant-based product, foam, wipe or solid. The cosmetically-acceptable carrier of the present invention is frequently formulated as an emulsion. The preferred emulsion is an oil-in-water emulsion. Silicones, such as volatile silicones and alkylated derivatives of polymeric silicones (hydrogenated polyisobutene, cyclomethicone and cetyl dimethicone), may be included in the formulations. As used herein, the cosmetically-acceptable carrier can include optional ingredients known to those skilled in the art, used at their art-established levels, including, but not limited to, preservatives, fragrances, emollients, anti-inflammatories, stabilizers, anti-bacterials, emulsifiers, and other suitable ingredients found in the Personal Care Product Council (PCPC) International Cosmetic Ingredients Dictionary (The Personal Care Products Council, Washington, D.C.), incorporated herein by reference.

The skin-tanning compositions of the present invention, particularly those utilizing dihydroxyacetone, may also contain one or more skin penetration enhancers. An acceptable amount of a skin penetration enhancer is from about 0.5% to about 20% of the composition. As used herein, a penetration enhancer is a material capable of aiding the penetration of the skin-tanning agent into the skin so that a deeper, longer-lasting artificial tan can be achieved. Examples of skin penetration enhancers include, but are not limited to, dimethyl isosorbide, caprylyl pyrrolidone, benzyl alcohol, propylene carbonate, lauryl pyrrolidone, benzyl oxyethanol, gamma-butyrol lactone, phenylethanol, and diethyl-glycol-monoethylether.

Various optional ingredients may be included in the compositions of the present invention for their conventional uses at their art-established usage levels; these include, but are not limited to, perfumes, sunscreens, amino acids, preservatives, emollients, antiseptics, anti-bacterials, stabilizers, anti-oxidants, vitamins, pigments, dyes, humectants, and propellants, as well as other classes of materials whose presence may be cosmetically, medicinally or otherwise desirable. Common examples of such ingredients are provided below by way of example and not limitation.

Optional ingredients can include polyoxyethylene ethers, such as PPG-12-buteth-16, PPG-3-buteth-5, PPG-5-buteth-7, PPG-7-buteth-10, PPG-9-buteth-12, PPG-12-buteth-16, PPG-15-buteth-20, PPG-20-buteth-30, PPG-28-buteth-35, PPG-33-buteth-45, PEG-4, PEG-6, PEG-8, PEG-10, PEG-12, PEG-32, or other suitable ingredients which provide emolliency; hydrolyzed wheat protein/wheat oligosaccharides, such as Cropeptide W, hydrolyzed corn protein, hydrolyzed wheat gluten, hydrolyzed yeast protein, hydrolyzed vegetable protein, hydrolyzed soy protein, hydrolyzed rice protein, hydrolyzed potato protein, other materials which provide moisturization; polyethylene glycol esters, such as PEG-14 laurate, PEG-15 laurate, PEG-20 laurate, PEG-32 laurate, PEG-75 laurate, PEG-150 laurate or other surfactants which are used for product formulation or fragrance solubilization; glycereth-7-triacetate (Dermol GL-7-A, Alza), glycerin, glycereth-5-lactate, glycereth-7-diisononanoate, which are used for moisturization, emolliency and to help solubilize fragrance; PEG-40 castor oil (Surfactol 365, Caschem), PEG-45 castor oil, PEG-50 castor oil, PEG-60 castor oil, PEG-100 castor oil, which are surfactants used to help solubilize fragrance and also to provide emolliency and moisturization; preservatives, such as methyldibromo-glutaronitrile-phenoxyethanol/polyquaternium-7 (Euxyl K-400, Calgon), methyl paraben, imidazolidinyl urea, benzalkonium chloride, diazolidinyl urea, benzethonium chloride, sodium benzoate and sorbic acid; sunscreens, such as octyldimethyl PABA, benzophenone-4, DEA methoxycinnamate, 2-phenyl-benzimidazole-5-sulfonic acid, and TEA salicylate; and fragrances.

The skin-tanning compositions of the present invention are suitable for use on human epidermis (skin). In order to achieve an acceptable amount of coloration of a person's skin, a person who desires such coloration or tan must evenly apply an effective amount of the skin coloring composition on the desired body surface area. Thus, the compositions can be formulated to provide the user with subtle changes in skin color, or more dramatic effects. The compositions will provide an artificial tan on the skin while reducing the unpleasant odor normally associated with the reaction between the skin-tanning agent and the skin.

The compositions of the present invention can be stored at room temperature between uses without significant or rapid degradation of the active components, which is known to sometimes occur with skin-tanning compositions.

A preferred process for preparing an oil-in-water emulsion composition of the present invention is as follows:
1. To an appropriately sized vessel to hold the entire batch, add DI water and start prop mixing to a medium vortex.
2. Add starch to the DI water and mix for 10 minutes. Start heating to 75-80° C. Add remainder of the water phase ingredients.
3. In a separate vessel, add the oil phase ingredients and heat to 75-80° C. Mix and melt the ingredients until clear and homogeneous.
4. When both oil phase and water phase reach 75-80° C., add oil phase to the water phase and increase agitation. Mix for 15 minutes. Start slow cooling to 60° C.

5. When both reach 60° C., add thickener and mix vigorously until homogeneous for 20-30 minutes. Start cooling to 40° C.
6. When both reach 40° C., slowly add dihydroxyacetone and mix for 10 minutes.
7. Fill into desired packaging.

Another process for preparing an oil-in-water emulsion composition of the present invention is as follows:
1. To an appropriately sized vessel to hold the entire batch, add DI water and start prop mixing to a medium vortex.
2. Start heating to 75-80° C. Add the remainder of the water phase ingredients.
3. In a separate vessel, add oil phase ingredients (including starch) and heat to 75-80° C. Mix and melt the ingredients until clear and homogeneous.
4. When both the oil phase and the water phase reach 75-80° C., add oil phase to water phase and increase agitation. Mix for 15 minutes. Start slow cooling to 60° C.
5. When batch reaches 60° C., add thickener and mix vigorously until homogeneous for 20-30 minutes. Start cooling to 40° C.
6. When batch reaches 40° C., slowly add dihydroxyacetone and mix for 10 minutes.
7. Fill into desired packaging.

In these processes, the heating of the starch component results in the expanded starch used in the present invention. Thus, heating of the starch in water or oil to a temperature of from about 50° C. to about 90° C., preferably from about 70° C. to about 80° C., for from about 10 minutes to about 3 hours (preferably in water for about 15 to about 60 minutes), will provide the expanded starch. High energy input, such as high shear mixing or fluidizing, may additionally be used together with the heating.

A methodology for determining malodor intensity in self-tanning compositions is as follows:

Determination of Malodor Intensity

Malodor intensity is determined by conducting an odor evaluation of each sample. During the odor evaluation, the presence of individual characteristic odors is investigated by a trained odor expert. The expert can determine the overall intensity of each odorant as well as how much each odorant contributes to the total intensity of the malodor. This leads to calculation of the reaction odor index (ROI) for each individual characteristic odor (equation 1). An example of an individual characteristic odor is burnt sugar or burnt caramel which is well known as a smell that contributes to sunless tanner odor.

Equation 1: Reaction Odor Index, ROI, is given by the following equation:

$$ROI_i = (\text{Individual Character Odor},i)(\% \text{ Contribution of Character Odor},i)$$

Equation 2: The Malodor Intensity Score (MIS) can then be calculated:

$$MIS = \Sigma ROI_i$$

Ideally, the total malodor intensity score, based on the ROI summation, should be less than or equal to 1.5. The table below provides examples of individual ROI numbers and the resulting Malodor Intensity Score.

| EXAMPLE | $ROI_A$ | $ROI_B$ | $ROI_C$ | $ROI_D$ | MIS | Comments |
|---|---|---|---|---|---|---|
| A | 1.4 | — | 1.1 | 1.1 | 3.5 | Does not contain amylopectin |
| B | 1.0 | — | 0.8 | 0.2 | 2 | |
| C | 1.2 | — | — | 0.8 | 2 | |
| D | 0.8 | — | — | 0.8 | 1.5 | |
| E | 0.6 | — | — | 0.4 | 1 | |
| F | 0.5 | — | — | 0.5 | 1 | |
| G | 0.3 | — | 0.3 | — | 0.5 | |
| H | 0.5 | — | — | — | 0.5 | |

The following examples are given to illustrate the present invention. Because these examples are given for illustrative purposes only, the invention should not be inferred to be limited to these examples.

EXAMPLES

Lotion (oil-in-water emulsion) compositions of the present invention, having the formulations given below, are prepared as described.

Example 1

| Part | INCI Name (% activity) | % weight |
|---|---|---|
| A | Water | Q.S. |
| | Methylparaben | 0.100-0.500 |
| | Ethylparaben | 0.100-0.500 |
| | Propylparaben | 0.100-0.500 |
| B | Glycerin | 1.000-10.000 |
| | Xanthan Gum | 0.100-0.500 |
| C | C12-15 Alkyl Benzoate | 0.100-2.000 |
| | Isopropyl Isostearate | 0.000-2.000 |
| | Glyceryl Stearate (and) PEG-100 Stearate | 0.100-2.000 |
| | Glyceryl Stearate | 0.100-2.000 |
| | Steareth-2 | 0.100-2.000 |
| | Cetyl Alcohol | 0.100-2.000 |
| | Behenyl Alcohol | 0.100-2.000 |
| | Dimethicone | 0.100-2.000 |
| | Phenyl Trimethicone | 0.100-2.000 |
| | Tocopheryl Acetate | 0.010-2.000 |
| | Ethylhexyl Methoxycinnamate | 4.000-10.000 |
| | Benzophenone-3 | 1.000-4.000 |
| D | Aluminum Starch Octenylsuccinate or Amylopectin or Waxy Corn Starch or *Zea Mays* (Corn) Starch | 0.100-10.00 |
| E | Polyacrylamide (and) C13-14 Isoparaffin (and) Laureth-7 | 0.100-2.000 |
| F | Water | 0.100-2.000 |
| | Citric Acid | 0.010-0.050 |
| G | Water | 5.000-20.000 |
| | Erythrulose | 0.010-10.000 |
| | Dihydroxyacetone | 0.010-10.000 |
| H | Water | 0.100-0.500 |
| | Caramel | 0.010-0.100 |
| I | Fragrance | 0.100-1.000 |
| | DMDM Hydantoin | 0.100-0.500 |

Procedure for Making:

Part A—To an appropriately sized vessel to hold the entire batch, add DI Water, start heating to 75-81 C. After batch has heated to 75 C, add remaining ingredients of Part A one at a time and mix until parabens dissolve.

Part B—In a separate vessel, slurry xanthan gum in glycerin until well dispersed. Add Part B to Part A.

Part C—In a separate vessel, add ingredients of Part C and heat to 75-81 C. Mix and melt until homogeneous.

Part D—When Part C reaches 75-81 C. add starch in Part D to Part C and mix until well dispersed and Part CD reheats to 75-81 C. When both Part CD and Part AB reach 75-81 C, increase agitation, and mix for 15 minutes. Then, start cooling to 60 C.

Part E—When Part ABCD reaches 60 C, add ingredient in Part E to Part ABCD and mix for 20 minutes or until smooth. Then, continue cooling to 40 C.

Part F—In a separate vessel, premix ingredients of Part F. After Part ABCDE has cooled to 40 C, add Part F to Part ABCDE and mix for 5 minutes.

Part G—In a separate vessel, premix ingredients of Part G. When Part G is clear and homogeneous, add to Part G to Part ABCDEF and mix for 10 minutes.

Part H—In a separate vessel, premix ingredients of Part H. Add Part H to Part ABCDEFG and mix for 5 minutes.

Part I—Add ingredients of Part I to Part ABCDEFGH one at a time and mix for 15 minutes.

Example 2

| Part | INCI Name (% activity) | % weight |
|---|---|---|
| A | Water | Q.S. |
|   | Aluminum Starch Octenylsuccinate or Amylopectin or Waxy Corn Starch or Zea Mays (Corn) Starch | 0.100-10.000 |
|   | Methylparaben | 0.100-0.500 |
|   | Ethylparaben | 0.100-0.500 |
|   | Propylparaben | 0.100-0.500 |
| B | Glycerin | 1.000-10.000 |
|   | Xanthan Gum | 0.100-0.500 |
| C | C12-15 Alkyl Benzoate | 0.100-2.000 |
|   | Isopropyl Isostearate | 0.000-2.000 |
|   | Glyceryl Stearate (and) PEG-100 Stearate | 0.100-2.000 |
|   | Glyceryl Stearate | 0.100-2.000 |
|   | Steareth-2 | 0.100-2.000 |
|   | Cetyl Alcohol | 0.100-2.000 |
|   | Behenyl Alcohol | 0.100-2.000 |
|   | Dimethicone | 0.100-2.000 |
|   | Phenyl Trimethicone | 0.100-2.000 |
|   | Tocopheryl Acetate | 0.010-2.000 |
|   | Ethylhexyl Methoxycinnamate | 4.000-10.000 |
|   | Benzophenone-3 | 1.000-4.000 |
| D | Polyacrylamide (and) C13-14 Isoparaffin (and) Laureth-7 | 0.100-2.000 |
| E | Water | 0.100-0.500 |
|   | Citric Acid | 0.010-0.050 |
| F | Water | 5.000-20.000 |
|   | Erythrulose | 0.010-10.000 |
|   | Dihydroxyacetone | 0.010-10.000 |
| G | Water | 0.100-0.500 |
|   | Caramel | 0.010-0.100 |
| H | Fragrance | 0.100-1.000 |
|   | DMDM Hydantoin | 0.100-0.500 |

Procedure for Making:

Part A—To an appropriately sized vessel to hold the entire batch, add DI Water and start prop mixing, then add starch and mix until well dispersed. Start heating to 75-81 C. After batch has heated to 75 C, add remaining ingredients of Part A one at a time and mix until parabens dissolve.

Part B—In a separate vessel, slurry xanthan gum in glycerin until well dispersed. Add Part B to Part A.

Part C—In a separate vessel, add ingredients of Part C and heat to 75 C. Mix and melt until homogeneous. When both Part C and Part AB reach 75 C, add Part C to Part AB, increase agitation, and mix for 15 minutes. Then, start cooling to 60 C.

Part D—When Part ABC reaches 60 C, add ingredient in Part D to Part ABC and mix for 20 minutes or until smooth. Then, continue cooling to 40 C.

Part E—In a separate vessel, premix ingredients of Part E. When Part ABCD has cooled to 40 C, add Part E to Part ABCD and mix for 5 minutes.

Part F—In a separate vessel, premix ingredients of Part F. When Part F is clear and homogeneous, add to Part ABCDE and mix for 10 mutes.

Part G—In a separate vessel, premix ingredients of Part G. Add Part G to Part ABCDEF and mix for 5 minutes.

Part H—Add ingredients of Part H to Part ABCDEFG, one at a time, and mix for 15 minutes.

Example 3

| Part | INCI Name (% activity) | % weight |
|---|---|---|
| A | Water | Q.S. |
|   | Aluminum Starch Octenylsuccinate or Amylopectin or Waxy Corn Starch or Zea Mays (Corn) Starch | 0.100-10.000 |
|   | Methylparaben | 0.100-0.500 |
|   | Ethylparaben | 0.100-0.500 |
|   | Propylparaben | 0.100-0.500 |
|   | Hydroxyethyl Acrylate/Sodium Acryloyldimethyl Taurate Copolymer (and) Isohexadecane (and) Polysorbate 60 | 0.100-2.000 |
| B | Glycerin | 1.000-10.000 |
|   | Xanthan Gum | 0.000-0.500 |
| C | Cetearyl Alcohol | 1.000-4.000 |
|   | Behenyl Alcohol | 0.000-2.000 |
|   | Stearic Acid | 0.000-2.000 |
|   | Mangifera Indica (Mango) Seed Butter | 0.000-1.000 |
|   | Petrolatum | 1.000-4.000 |
|   | Mineral Oil | 1.000-4.000 |
|   | Ceteareth-20 | 1.000-4.000 |
|   | Steareth-2 | 0.100-2.000 |
|   | Ethylhexyl Isononanoate | 0.100-2.000 |
|   | Octyldodecyl Myristate | 0.100-2.000 |
|   | Isopropyl Isostearate | 0.000-2.000 |
|   | Dimethicone | 0.100-2.000 |
| D | BHT | 0.010-0.500 |
| E | Water | 0.100-0.500 |
|   | Citric Acid | 0.010-0.050 |
| F | Water | 5.000-20.000 |
|   | Erythrulose | 0.010-10.000 |
|   | Dihydroxyacetone (and) Troxerutin | 0.000-10.000 |
|   | Dihydroxyacetone | 0.010-10.000 |
| G | Water | 0.100-0.500 |
|   | Caramel | 0.010-0.100 |
| H | Fragrance | 0.100-1.000 |
|   | Olea Europaea (Olice) Fruit Oil (and) Avena Sativa (Oat) Kernel Extract (and) Calendule Officinalis Flower Extract (and) Persea Gratissima (Avocado) Oil (and) Simmondsia Chinensis (Jojoba) Seed Oil (and) Tocopherol | 0.000-1.000 |
|   | Polyimide-1 | 0.000-1.000 |
|   | Hydrolyzed Elastin | 0.000-1.000 |
|   | Hydrolyzed Collagen | 0.000-1.000 |
|   | Water (and) Butylene Glycol (and) Fucus Vesiculosus Extract | 0.000-1.000 |
|   | Water (and) Butylene Glycol (and) Hydrocotyl (Centella Asiatica) Extract | 0.000-1.000 |
|   | Cocos Nucifera (Coconut) Water (and) Withania Somnifera Root Extract | 0.000-1.000 |
|   | Tocopherol | 0.000-1.000 |
|   | DMDM Hydantoin | 0.100-0.500 |

Procedure for Making:

Part A—To an appropriately sized vessel to hold the entire batch, add DI Water and start prop mixing, then add glycerin and starch and mix until well dispersed. Start heating to 75-81 C. After batch has heated to 75 C, add parabens in Part A and mix until they dissolve. Then, add last ingredient of Part A and mix for 20 minutes or until smooth.

Part B—In a separate vessel, slurry xanthan gum in glycerin until well dispersed. Add Part B to Part A.

Part C—In a separate vessel, add ingredients of Part C and heat to 75-81 C. Mix and melt until homogeneous.

Part D—When Part C reaches 75-81 C, add ingredient of Part D to Part C and melt until homogeneous, then add Part CD to Part AB. Increase agitation and mix for 15 minutes. Then, start cooling to 40 C.

Part E—In a separate vessel, premix ingredients of Part E. After Part ABCD reaches 40 C, add Part E to Part ABCD and mix for 5 minutes.

Part F—In a separate vessel, premix ingredients of Part F. When Part F is clear and homogeneous, add Part F to Part ABCDE and mix for 10 minutes.

Part G—In a separate vessel, premix ingredients of Part G. Add Part G to Part ABCDEF and mix for 5 minutes.

Part H—Add ingredients of Part H to Part ABCDEFG, one at a time, and mix for 15 minutes.

Example 4

| Part | INCI Name (% activity) | % weight |
|---|---|---|
| A | Water | Q.S. |
|  | Methylparaben | 0.100-0.500 |
|  | Ethylparaben | 0.100-0.500 |
|  | Propylparaben | 0.100-0.500 |
|  | Hydroxyethyl Acrylate/Sodium Acryloyldimethyl Taurate Copolymer (and) Isohexadecane (and) Polysorbate 60 | 0.100-2.000 |
| B | Glycerin | 1.000-10.000 |
|  | Xanthan Gum | 0.000-0.500 |
| C | Cetearyl Alcohol | 1.000-4.000 |
|  | Behenyl Alcohol | 0.000-2.000 |
|  | Stearic Acid | 0.000-2.000 |
|  | *Mangifera Indica* (Mango) Seed Butter | 0.000-1.000 |
|  | Petrolatum | 1.000-4.000 |
|  | Mineral Oil | 1.000-4.000 |
|  | Ceteareth-20 | 1.000-4.000 |
|  | Steareth-2 | 0.100-2.000 |
|  | Ethylhexyl Isononanoate | 0.100-2.000 |
|  | Octyldodecyl Myristate | 0.100-2.000 |
|  | Isopropyl Isostearate | 0.000-2.000 |
|  | Dimethicone | 0.100-2.000 |
| D | BHT | 0.010-0.500 |
|  | Aluminum Starch Octenylsuccinate or Amylopectin or Waxy Corn Starch or *Zea May* (Corn) Starch | 0.100-10.000 |
| E | Water | 0.100-0.500 |
|  | Citric Acid | 0.010-0.050 |
| F | Water | 5.000-20.000 |
|  | Erythrulose | 0.010-10.000 |
|  | Dihydroxyacetone (and) Troxerutin | 0.000-10.000 |
|  | Dihydroxyacetone | 0.010-10.000 |
| G | Water | 0.100-0.500 |
|  | Caramel | 0.010-0.100 |
| H | Fragrance | 0.100-1.000 |
|  | *Olea Europaea* (Olice) Fruit Oil (and) *Avena Sativa* (Oat) Kernel Extract (and) *Calendule Officinalis* Flower Extract (and) *Persea Gratissima* (Avocado) Oil (and) *Simmondsia Chinensis* (Jojoba) Seed Oil (and) Tocopherol | 0.000-1.000 |
|  | Polyimide-1 | 0.000-1.000 |
|  | Hydrolyzed Elastin | 0.000-1.000 |
|  | Hydrolyzed Collagen | 0.000-1.000 |
|  | Water (and) Butylene Glycol (and) *Fucus Vesiculosus* Extract | 0.000-1.000 |
|  | Water (and) Butylene Glycol (and) Hydrocotyl (*Centella Asiatica*) Extract | 0.000-1.000 |
|  | *Cocos Nucifera* (Coconut) Water (and) *Withania Somnifera* Root Extract | 0.000-1.000 |
|  | Tocopherol | 0.000-1.000 |
|  | DMDM Hydantoin | 0.100-0.500 |

Procedure:

Part A—To an appropriately sized vessel to hold the entire batch, add DI Water, start prop mixing, then add glycerin and mix until well dispersed. Start heating to 75-81 C. After batch has heated to 75 C, add parabens in Part A and mix until they dissolve. Then, add last ingredients of Part A and mix for 20 minutes or until smooth.

Part B—In a separate vessel, slurry xanthan gum in glycerin until well dispersed. Add Part B to Part A.

Part C—In a separate vessel, add ingredients of Part C and heat to 75-81 C. Mix and melt until homogeneous.

Part D—When Part C reaches 75-81 C, add ingredient of Part D to Part C one at a time and mix until well dispersed and Part CD reheats to 75-81 C. Then, add Part CD to Part AB, increase agitation and mix for 15 minutes. Then, start cooling to 40 C.

Part E—In a separate vessel, premix ingredients of Part E. After Part ABCD has cooled to 40 C, add Part E to Part ABCD and mix for 5 minutes.

Part F—In a separate vessel, premix ingredients of Part F. When Part F is clear and homogeneous, add Part F to Part ABCDE and mix for 10 minutes.

Part G—In a separate vessel, premix ingredients of Part G. Add Part G to Part ABCDEF and mix for 5 minutes.

Part H—Add ingredients of Part H to Part ABCDEFG and mix for 15 minutes.

The compositions, described above, when applied in an effective amount to an area of human skin, provide the appearance of tanning to that skin while significantly reducing the unpleasant odors which can sometimes result from the Maillard reaction which occurs when self-tanning compositions are applied to the skin.

What is claimed is:

1. A skin-tanning composition which comprises:
   (a) from about 0.1% to about 20% of a skin-tanning agent selected from dihydroxyacetone, erythrulose, and mixtures thereof;
   (b) from about 0.1% to about 10% of an odor-mitigating material selected from starch-based polysaccharides that contain at least 50% amylopectin and which are treated such that their crystal structure is not present; and
   (c) a cosmetically acceptable carrier;
   wherein the starch-based polysaccharide is selected from waxy maize starch, aluminum starch octenylsuccinate, corn starch, and mixtures thereof.

2. The skin-tanning composition of claim 1 wherein the polysaccharide contains at least 70% amylopectin.

3. The skin-tanning composition of claim 1 wherein the polysaccharide is treated by heating in a solvent to a temperature of from about 50° C. to about 90° C. for a period of from about 5 minutes to about 24 hours.

4. The skin-tanning composition of claim 1, which includes from about 1% to about 10% of the odor-mitigating material.

5. The skin-tanning composition according to claim 4, which contains from about 3% to about 7% of the odor-mitigating material.

6. The skin-tanning composition according to claim 1, which includes from about 2% to about 8% odor-mitigating material.

7. The skin-tanning composition according to claim 4, wherein the composition is formulated as an emulsion, gel, spray, foam, wipe, liquid, solid, or powder.

8. The skin-tanning composition according to claim 7, wherein the composition is formulated as an oil-in-water emulsion.

9. The skin-tanning composition according to claim 1, which includes from about 0.1% to about 10% of the skin-tanning agent.

10. The skin-tanning composition of claim 1 wherein the odor-mitigating material is corn starch.

11. A method of reducing the Maillard reaction odor generated when a sunless tanning composition, containing a skin-tanning agent selected from dihydroxyacetone, erythrulose, and mixtures thereof, is applied to the skin, comprising including in said composition from about 0.1% to about 10% of an odor-mitigating material selected from starch-based polysaccharides that contain at least 50% amylopectin, wherein the polysaccharide is treated such that its crystal structure is not present;
    wherein the starch-based polysaccharide is selected from waxy maize starch, aluminum starch octenylsuccinate, corn starch, and mixtures thereof.

12. The method according to claim 11, which utilizes from about 1% to about 10% odor-mitigating material.

13. A method of providing an artificial tan to human skin which comprises applying an effective amount of the composition of claim 1 to the skin.

14. A method of providing an artificial tan to human skin which comprises applying an effective amount of the composition of claim 6 to the skin.

15. A method for making the composition of claim 1 wherein the starch is heated in water to a temperature of from about 70° C. to about 80° C., for from about 10 to about 60 minutes, adding said water phase to an oil phase with stirring to form an emulsion, and then adding the skin-tanning agent to said emulsion.

16. The method of claim 15 wherein the water phase is heated to about 75-80° C.

17. The method of claim 16 wherein the water phase is subjected to high shear mixing during the heating step.

* * * * *